US007628752B2

United States Patent
Yamamoto et al.

(10) Patent No.: US 7,628,752 B2
(45) Date of Patent: Dec. 8, 2009

(54) IMAGE CAPTURING UNIT FOR ELECTRONIC ENDOSCOPE

(75) Inventors: Kazuyuki Yamamoto, Saitama (JP); Takayuki Ogino, Saitama (JP); Akihiro Ito, Saitama (JP); Seiichiro Okamura, Ibaraki (JP); Tomokazu Yamashita, Ibaraki (JP)

(73) Assignee: Hoya Corporation, Tokyo (JP)

( * ) Notice: Subject to any disclaimer, the term of this patent is extended or adjusted under 35 U.S.C. 154(b) by 242 days.

(21) Appl. No.: 11/456,281

(22) Filed: Jul. 10, 2006

(65) Prior Publication Data
US 2007/0010706 A1 Jan. 11, 2007

(30) Foreign Application Priority Data
Jul. 11, 2005 (JP) ............................. 2005-201112

(51) Int. Cl.
  *A61B 1/05* (2006.01)
  *A61B 1/04* (2006.01)
(52) U.S. Cl. ....................................... 600/109; 348/340
(58) Field of Classification Search ................. 600/109, 600/110; 348/65, 76, 272, 294, 340
See application file for complete search history.

(56) References Cited

U.S. PATENT DOCUMENTS

| 4,725,126 | A | * | 2/1988 | Siga et al. ................... 359/819 |
| 4,745,470 | A | * | 5/1988 | Yabe et al. .................... 348/76 |
| 4,778,253 | A | * | 10/1988 | Siga et al. ................... 359/819 |
| 4,805,598 | A | * | 2/1989 | Ueda ........................... 600/169 |
| 4,841,952 | A | * | 6/1989 | Sato et al. ................... 600/129 |
| 5,291,010 | A | * | 3/1994 | Tsuji ....................... 250/208.1 |
| 6,564,018 | B2 | * | 5/2003 | Melman et al. ............. 396/429 |
| 6,695,775 | B2 | * | 2/2004 | Watanabe et al. ........... 600/176 |
| 7,022,066 | B2 | * | 4/2006 | Yokoi et al. ................. 600/109 |
| 7,375,757 | B1 | * | 5/2008 | Hoshino et al. ............. 348/340 |
| 7,379,113 | B2 | * | 5/2008 | Kong et al. ................. 348/340 |
| 2003/0156213 | A1 | * | 8/2003 | Doering et al. ............. 348/340 |

(Continued)

FOREIGN PATENT DOCUMENTS

JP 7-226493 8/1995

(Continued)

OTHER PUBLICATIONS

English language Abstract of JP 2000-060793.

(Continued)

*Primary Examiner*—John P Leubecker
(74) *Attorney, Agent, or Firm*—Greenblum & Bernstein, P.L.C.

(57) ABSTRACT

An image capturing unit for an electronic endoscope is provided with a solid-state image capturing element having multiple boding wires arranged at peripheral positions on a front surface of the solid-state image capturing element, the bonding wires extending outward, an image capturing element holding frame in which the solid-state image capturing element is held and a transparent cover glass enclosing the front surface of the solid-state image capturing element from outside, together with a tip end portion of the image capturing element holding frame. The tip end portion of the image capturing element holding frame is formed to have a tubular section, the cover glass being fitted in the tubular section and located at a position where the cover glass does not contact the bonding wires, the cover glass being air-tightly cemented to the tubular section.

2 Claims, 11 Drawing Sheets

U.S. PATENT DOCUMENTS

| | | |
|---|---|---|
| 2005/0174469 A1* | 8/2005 | Cho et al. .................... 348/340 |
| 2005/0190284 A1* | 9/2005 | Wakano et al. .............. 348/340 |
| 2006/0152615 A1* | 7/2006 | Kwon et al. ................. 348/340 |
| 2006/0181633 A1* | 8/2006 | Seo ............................. 348/340 |
| 2007/0058069 A1* | 3/2007 | Chen et al. .................. 348/340 |
| 2008/0106624 A1* | 5/2008 | Webster ...................... 348/294 |

FOREIGN PATENT DOCUMENTS

| | | |
|---|---|---|
| JP | 2000-060793 | 2/2000 |
| JP | 2003-100920 | 4/2003 |
| JP | 2003-258221 | 9/2003 |

OTHER PUBLICATIONS

English language Abstract of JP 2003-258221.
English language Abstract of JP 2003-100920.
English language Abstract of JP 7-226493.
U.S. Appl. No. 11/427,812 to Ogino et al., which was filed on Jun. 30, 2006.
U.S. Appl. No. 11/456,253 to Yamamoto et al., which was filed on Jul. 10, 2006.
U.S. Appl. No. 11/456,288 to Yamamoto et al., which was filed on Jul. 10, 2006.

* cited by examiner

IMAGE CAPTURING UNIT FOR ELECTRONIC ENDOSCOPE

BACKGROUND OF THE INVENTION

The present invention relates to an image capturing unit for an electronic endoscope which is built in at a distal end portion of an insertion section of the electronic endoscope.

Generally, the image capturing unit for the electronic endoscope is configured such that a solid-state image capturing element is held by a holding frame. The solid-state image capturing element is configured such that, on a front surface having an image capturing surface, boding wires are arranged at peripheral positions thereof to extend in outer directions, The solid-state image capturing element is held at a tip portion of the holding frame. Further, a transparent cover glass is air-tightly attached to the front end (tip end) of the holding frame so that steam or water does not enter even when the endoscope is placed inside a high-temperature high-pressure steam sterilizer or the like. Examples of such a configuration are disclosed in Japanese Patent Provisional Publications Nos. P2003-100920A and HEI 07-226493.

FIG. 6 shows an example of a conventional image capturing unit for the electronic endoscope. In this example, a cover glass 93 is directly cemented onto the tip end surface of a solid-state image capturing element holding frame 92 that holds the solid-state image capturing element 91. In FIG. 6, 91a denotes an image capturing surface, and 94 denotes each of the bonding wires.

When the image capturing unit 90 as shown in FIG. 6 is implemented in an objective optical unit 80 including an objective optical system 81 as shown in FIG. 7, if a distance A between the image capturing surface 91a and the cover glass 93 is relatively large, a back focus B necessary for focus adjustment with respect to the objective optical system 81 becomes relatively short, and it sometimes becomes impossible to perform sufficient focus adjustment.

On the other hand, if the back focus B is increased with the distance A remained unchanged, it becomes necessary to increase the entire length of the insertion section of the endoscope. When the insertion section becomes long, it becomes difficult to insert the insertion section in a human cavity, and further, such a configuration has a bad effect on a basic performance of the endoscope.

Therefore, it is preferable to make the distance A as short as possible. However, if such a configuration is employed and the optical system is manufactured, due to unevenness of sizes, thickness and the like of components, the cover glass 93 may contact the bonding wires 94 as shown in FIG. 8. In such a case, the bonding wires 94 may be damaged.

FIG. 9 shows another example of a conventional image capturing unit for the electronic endoscope, in which the cover glass 93 is air-tightly cemented with a cover glass holding frame 95, which is air-tightly cemented with a solid-state image capturing element holding frame 92.

In this configuration, as shown in FIG. 10, if the distance A between the image capturing surface 91a and the cover glass 93 is reduced to avoid a problem when the image capturing unit 90 is assembled in the objective optical system unit 80, the cover glass 93 may contact the bonding wires 94 as shown in FIG. 11. Therefore, also in this case, the bonding wires 94 may be damaged.

SUMMARY OF THE INVENTION

The aspects of the present invention provide an image capturing unit for an electronic endoscope configured such that the a distance between the image capturing surface and a cover glass can be well reduced and the cover glass will not contact the bonding wires.

According to aspects of the invention, there is provided an image capturing unit for an electronic endoscope. The image capturing unit is provided with a solid-state image capturing element having multiple boding wires arranged at peripheral positions on a front surface of the solid-state image capturing element, the bonding wires extending outward, an image capturing element holding frame in which the solid-state image capturing element is held and a transparent cover glass enclosing the front surface of the solid-state image capturing element from outside, together with a tip end portion of the image capturing element holding frame. The tip end portion of the image capturing element holding frame is formed to have a tubular section, the cover glass being fitted in the tubular section and located at a position where the cover glass does not contact the bonding wires, the cover glass being air-tightly cemented to the tubular section.

The cover glass may be directly and air-tightly cemented on an inner surface of the tubular section of the holding frame. Alternatively, the cover glass may be air-tightly cemented to a cover glass holding frame, and the cover glass holding frame may be air-tightly cemented on the inner surface of the tubular section of the holding frame.

BRIEF DESCRIPTION OF THE ACCOMPANYING DRAWINGS

DETAILED DESCRIPTION OF THE EMBODIMENTS

Figure 1:
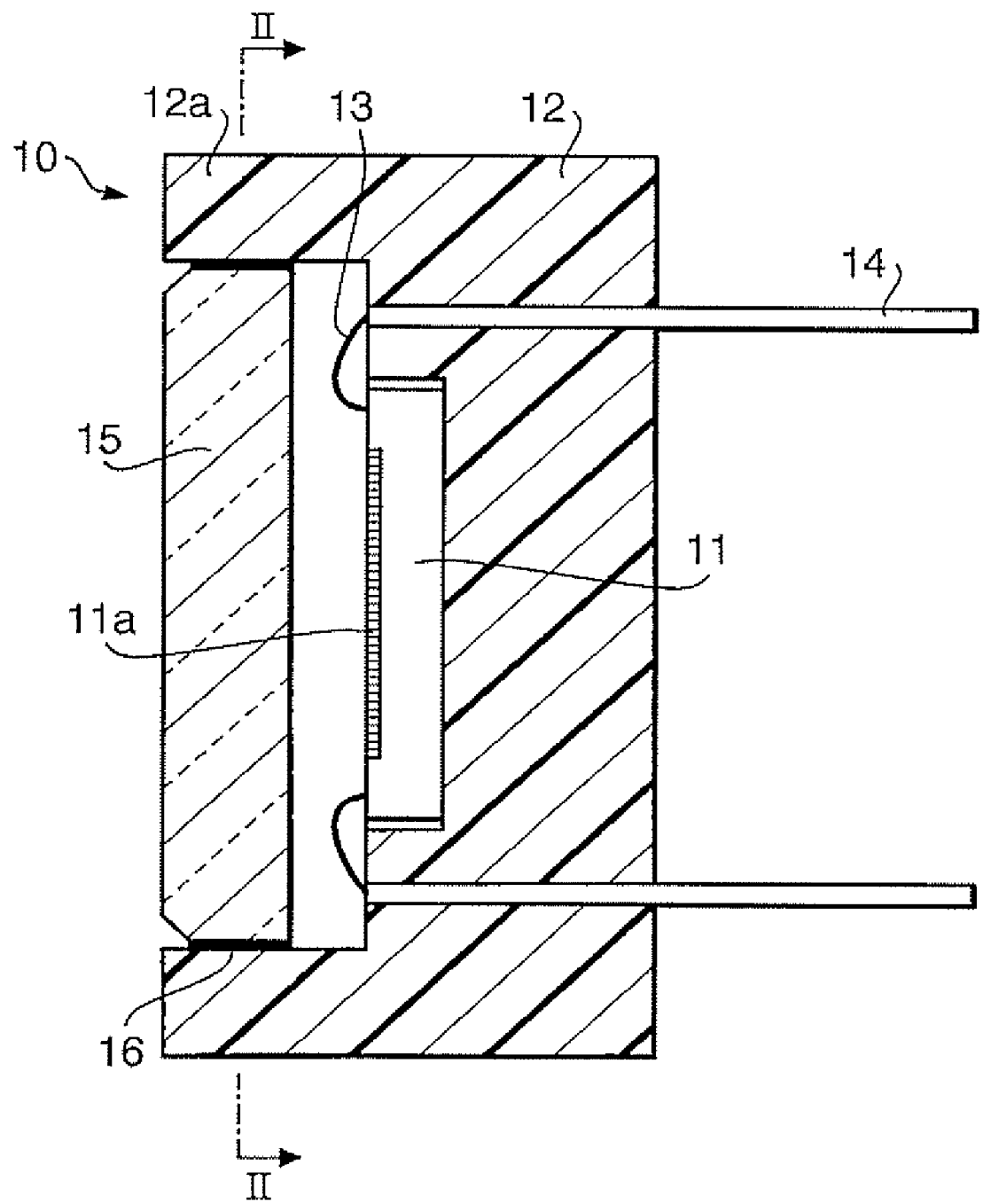
FIG. 1 is a cross-sectional side view of an image capturing unit according to a first embodiment of the invention.
Figure 2:
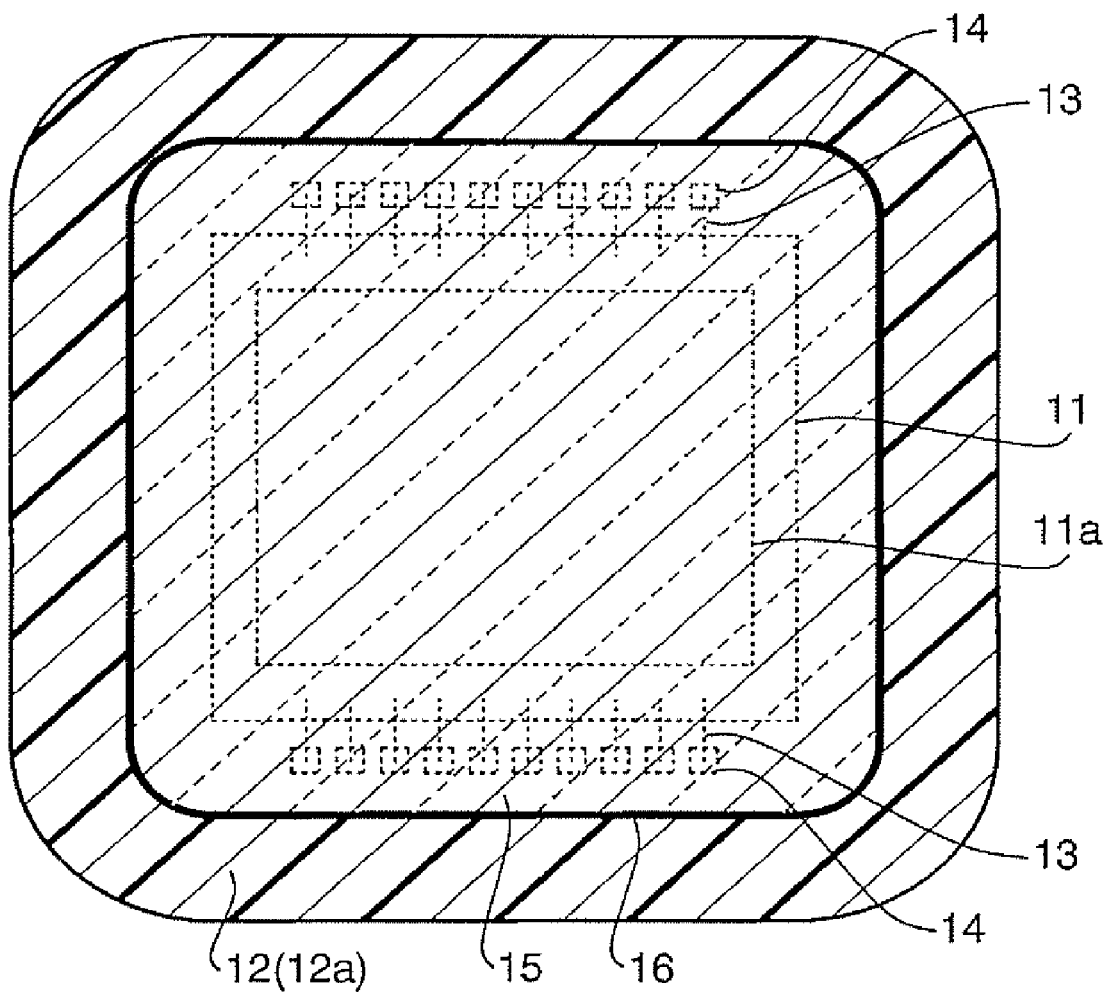
FIG. 2 is a cross-sectional view taken along line II-II of FIG. 1.

Hereinafter, referring to the accompanying drawings, image capturing unit according to embodiments of the invention will be described, FIG. 1 is a cross-sectional side view of an image capturing unit 10 for an electronic endoscope according to a first embodiment of the invention. FIG. 2 is cross-sectional view of the image capturing unit 10 taken along line II-II of FIG. 1. In the figures, 11 denote a solid-state image capturing element such as a CCD (Charge Coupled Device). On a front surface (i.e., a left-hand side surface) of the solid-state image capturing unit 11, at a central area thereof, an image capturing surface 11a is defined. The image capturing surface 11a is a rectangular area, which is smaller than the outline of the front surface of the solid-state image capturing element 11.

In FIG. 1, 12 denotes a holding frame having a rectangular parallelepiped solid shape made of electrically insulating material such as ceramic. On a front side surface (i.e., a left-hand side surface) of the holding frame 12, a recess is formed, in which the solid-state image capturing element 11 is fitted in and secured with adhesive agent so that only the front surface of the image capturing element 11 is exposed to outside.

The solid-state image capturing element 11 is arranged such that the image capturing surface 11a is recessed with respect to a tip end of the holding frame 12 in a direction of the central axis of the electronic endoscope. The distal end portion of the holding frame 12 is formed to have a tubular section 12a which has a substantially rectangular cross section and protrudes frontward with respect to the image capturing surface 11a.

There are multiple bonding wires 13 which connect tip ends of multiple lead terminals 14 with an inner circuit of the solid-state image capturing element 11, respectively. The lead terminals 14 are configured to extend (protrude) rearward from the holding frame 12. Specifically, the bonding wires 13 are arranged at upper and lower peripheral portions of the solid-state image capturing element 11 and extend outward (i.e., in upper and lower directions) as shown in FIGS. 1 and 2.

Each bonding wire 13 is arranged to be loosened and to form an arc protruding frontward from the front end surface of the solid-state image capturing element 11 toward a space in front thereof, then connected to a tip end of a corresponding lead terminal 14. Each lead terminal 14 extends rearward, penetrating through the holding frame 12 in the axial direction.

To an inner circumference of the tubular section 12a of the holding frame 12, a cover glass 15 made of transparent optical glass is fitted from outside (i.e., front side) and cemented so that the solid-state image capturing element 11 is air-tightly enclosed. In FIG. 1, 16 denotes the cemented portion. As shown in FIG. 1, the cover glass 15 is fitted in the inner circumferential portion of the tubular section 12a of the holding frame 12, and the outer circumferential surface of the cover glass 15 is air-tightly cemented with the inner circumference of the tubular section 12a with inorganic adhesive agent. With this configuration, even if it is placed inside the high-temperature, high-pressure steam sterilizer or the like, the steam or water will not enter inside the tubular section 12a. It is noted that, throughout this specification, a term "circumference" or "circumferential" is used to indicate a surface of a tubular section in a direction perpendicular to an axial direction thereof, regardless of whether the cross sectional shape of the tubular section is circular or rectangular.

The tubular section 12a is not formed with a positioning structure such as a step for positioning the cover glass 15 in the axial direction. When the cover glass 15 is cemented to the image capturing element holding frame 12, the position of the cover glass is appropriately adjusted such that the rear surface of the cover glass 15 is close to the image capturing surface 11a but does not contact the bonding wires 13, and then the cover glass 15 is air-tightly cemented to the tubular portion 12 with inorganic adhesive agent.

Figure 3:
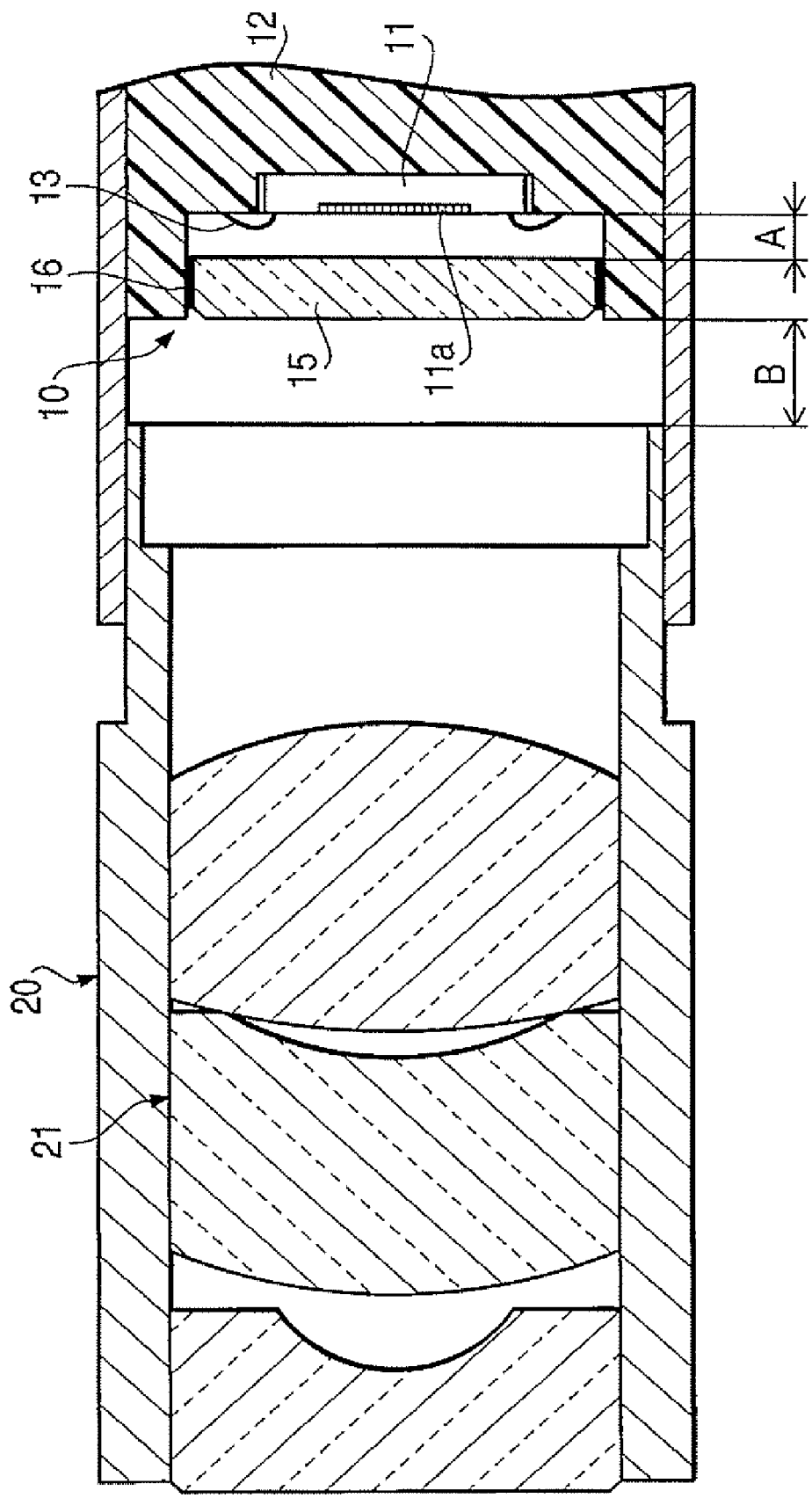
FIG. 3 is a cross-sectional side view showing the image capturing unit incorporated in an objective optical system unit, according to the first embodiment of the invention.

When the cover glass 15 is secured to the image capturing unit 10 in the above-described manner, the rear surface of the cover glass 15 will not contact the bonding wires 13. Therefore, the bonding wires 13 will not be damaged by the cover glass 15. In addition, as shown in FIG. 3, when the image capturing unit 10 is incorporated in the objective optical system unit 20 implemented with the objective optical system 21, the distance A between the image capturing surface 11a and the cover glass 15 is sufficiently small. Therefore, a sufficient back focus B necessary for adjusting focusing condition of the objective optical system 21 can be obtained.

Figure 4:
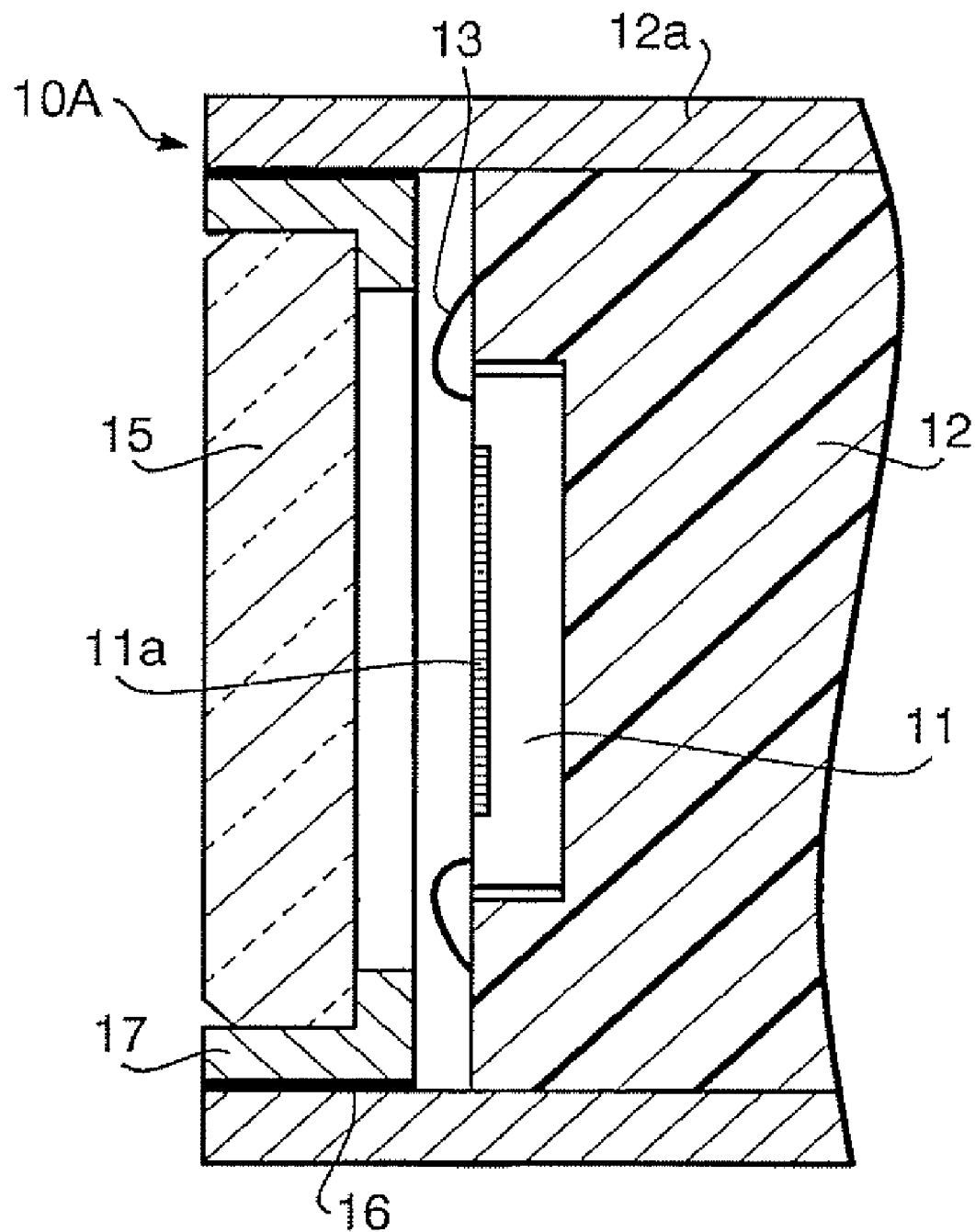
FIG. 4 is a cross-sectional side view of an image capturing unit according to a second embodiment of the invention.

FIG. 4 shows a cross-sectional side view of an image capturing unit 10A according to a second embodiment of the invention. As shown in FIG. 4, the image capturing unit 10A is provided with a cover glass frame 17, which is made of metal and has a U-shaped cross section, and has an opening at the central portion of a bottom surface thereof. The cover glass 15 is cemented to the cover glass frame 17 at the outer circumference and rear peripheral portion thereof with inorganic adhesive agent.

The cover glass frame 17 is fitted in the tubular section 12a of the holding frame 12. The best position, in the axial direction, of the cover glass frame 17 is determined such that the rear side of the cover glass 15 is sufficiently close to the image capturing surface 11a but does not contact the bonding wires 13. At the above-described position, the outer circumference of the cover glass frame 17 is cemented with the inner circumference of the tubular section 12a of the holding frame 12.

As material of the cover glass frame 17, alloy metal having the same CTE (coefficient of thermal expansion) as the cover glass 15 may be used. For example, Kover or 42 Alloy containing Nickel may be used. The tubular section 12a of the holding frame 12 may be made of the same material. At the cemented portion 16, the entire inner circumferential surface of the tubular section 12a and the entire outer circumferential surface of the cover glass frame 17 are air-tightly cemented with welding or soldering.

Figure 5:
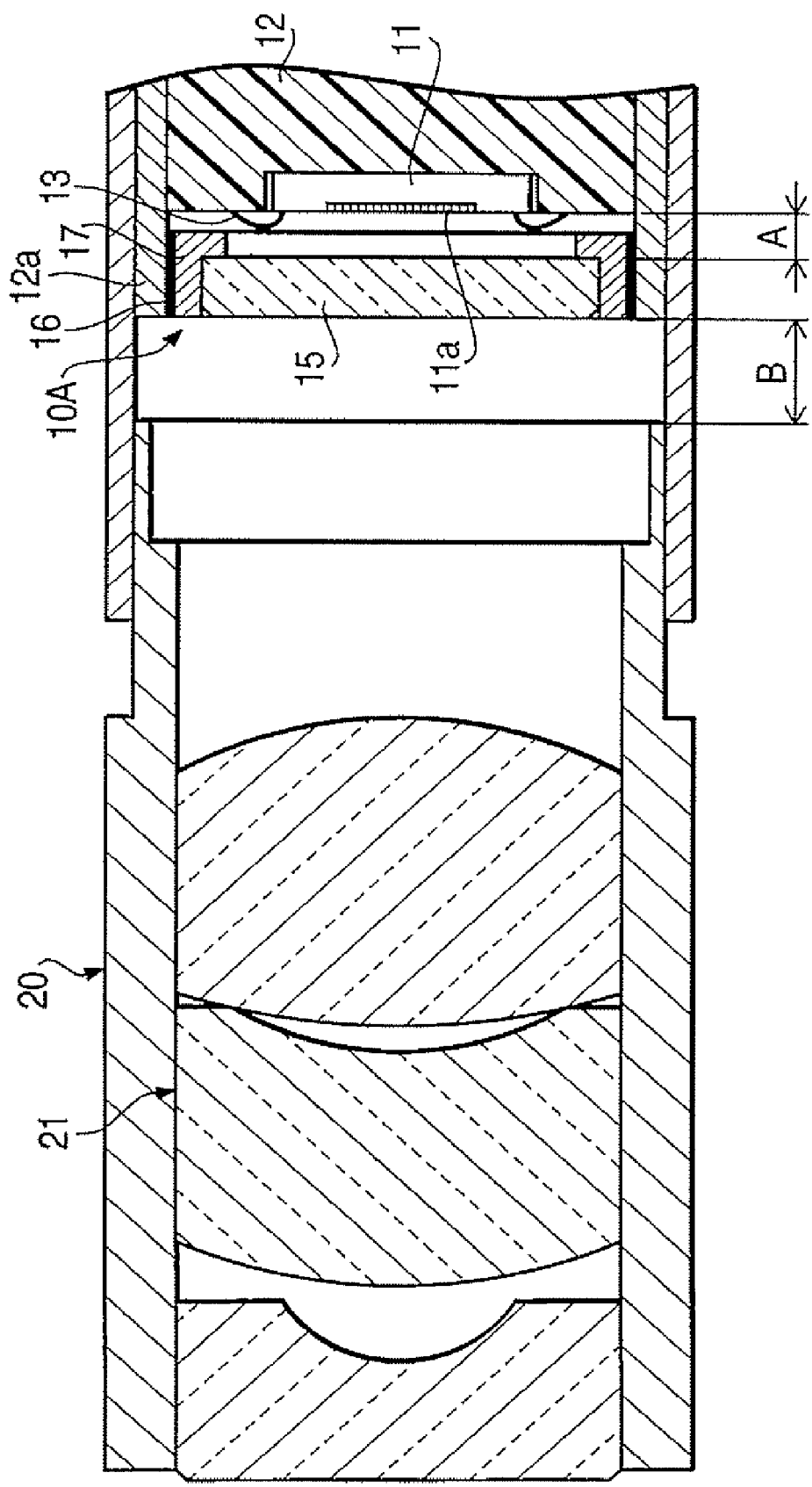
FIG. 5 is a cross-sectional side view showing the image capturing unit incorporated in an objective optical system unit, according to the second embodiment of the invention.
Figure 6:
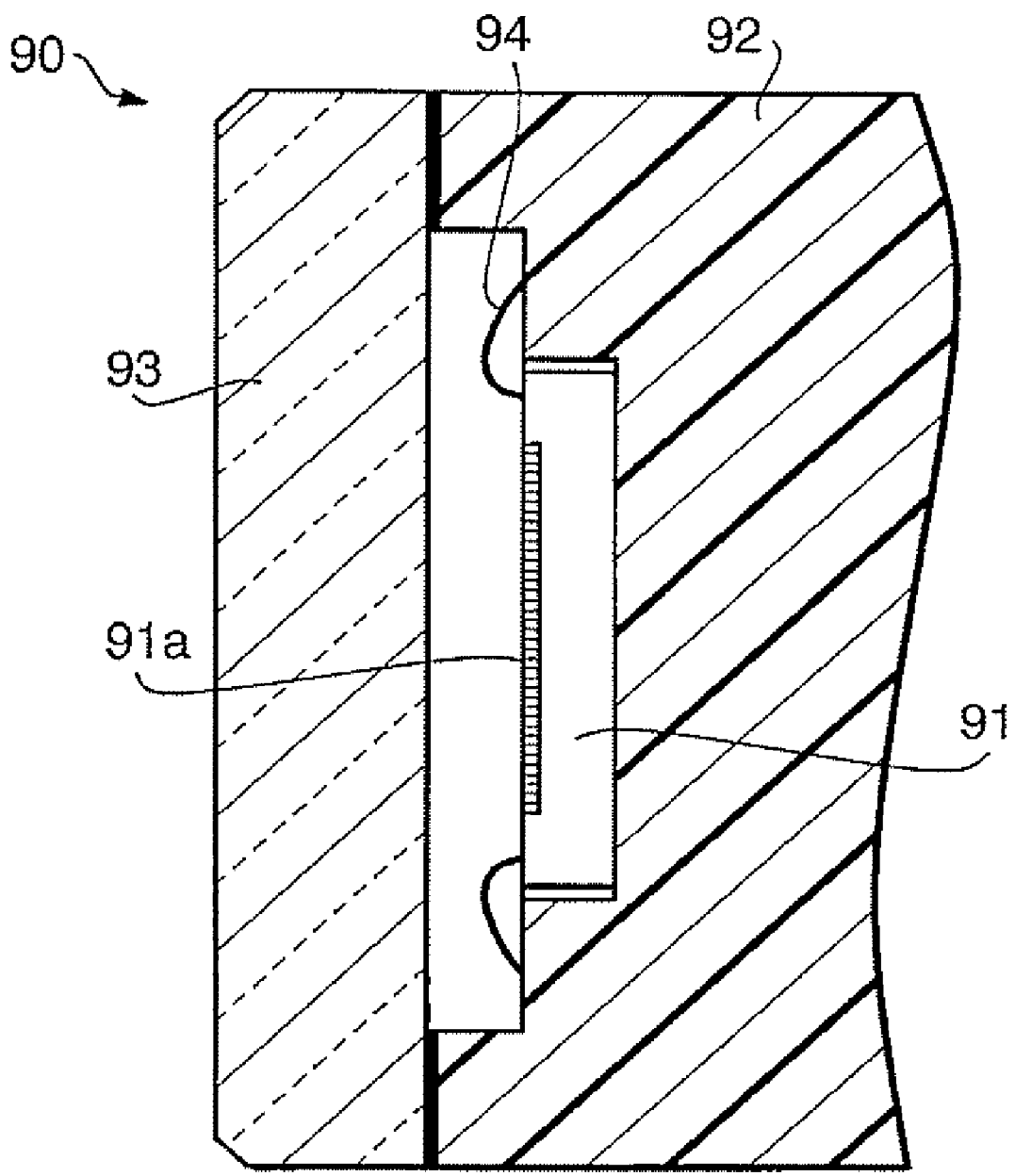
FIG. 6 is a cross-sectional side view of a conventional image capturing unit.
Figure 7:
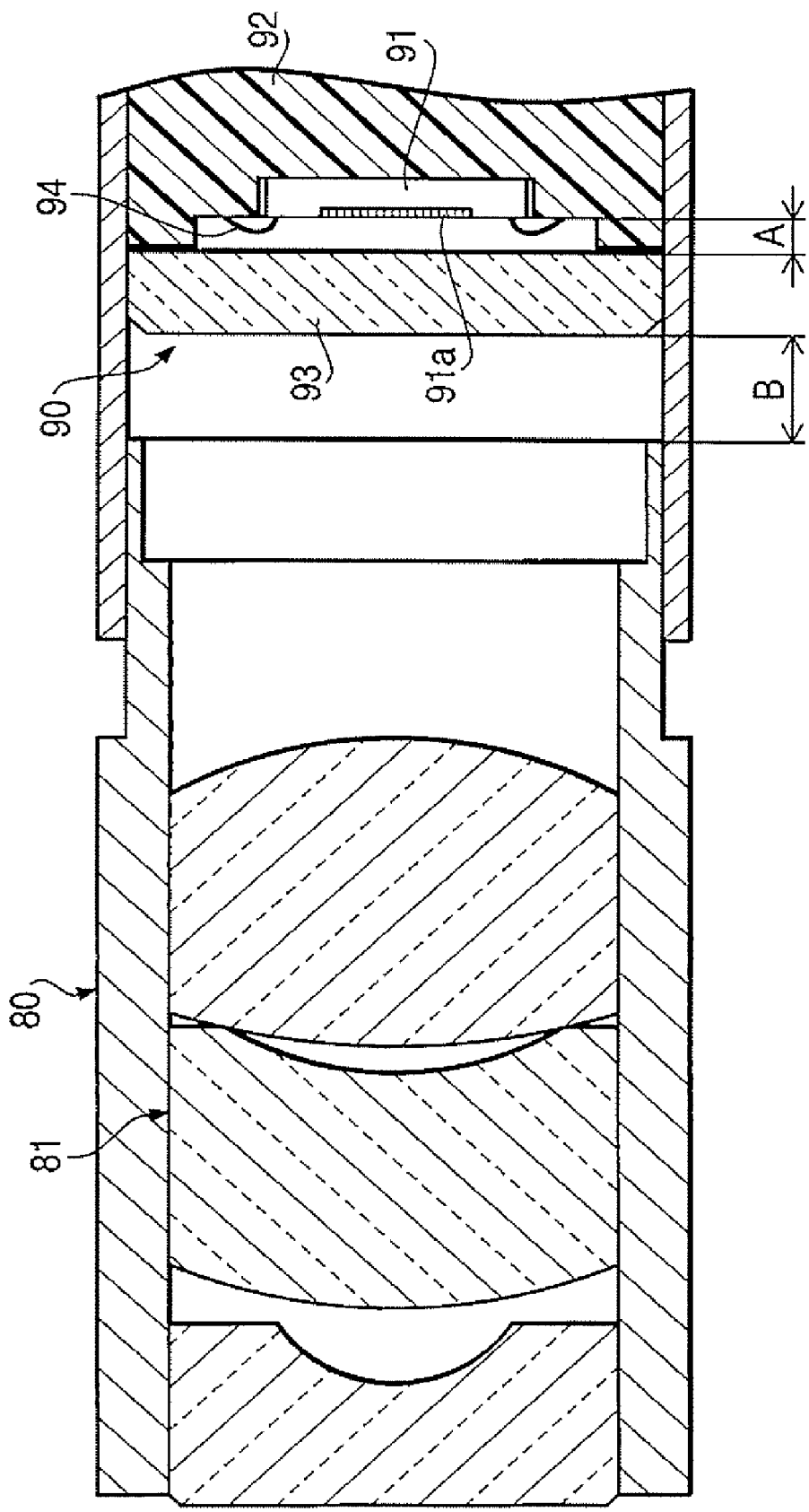
FIG. 7 is a cross-sectional side view showing the conventional image capturing unit incorporated in an objective optical system unit.
Figure 8:
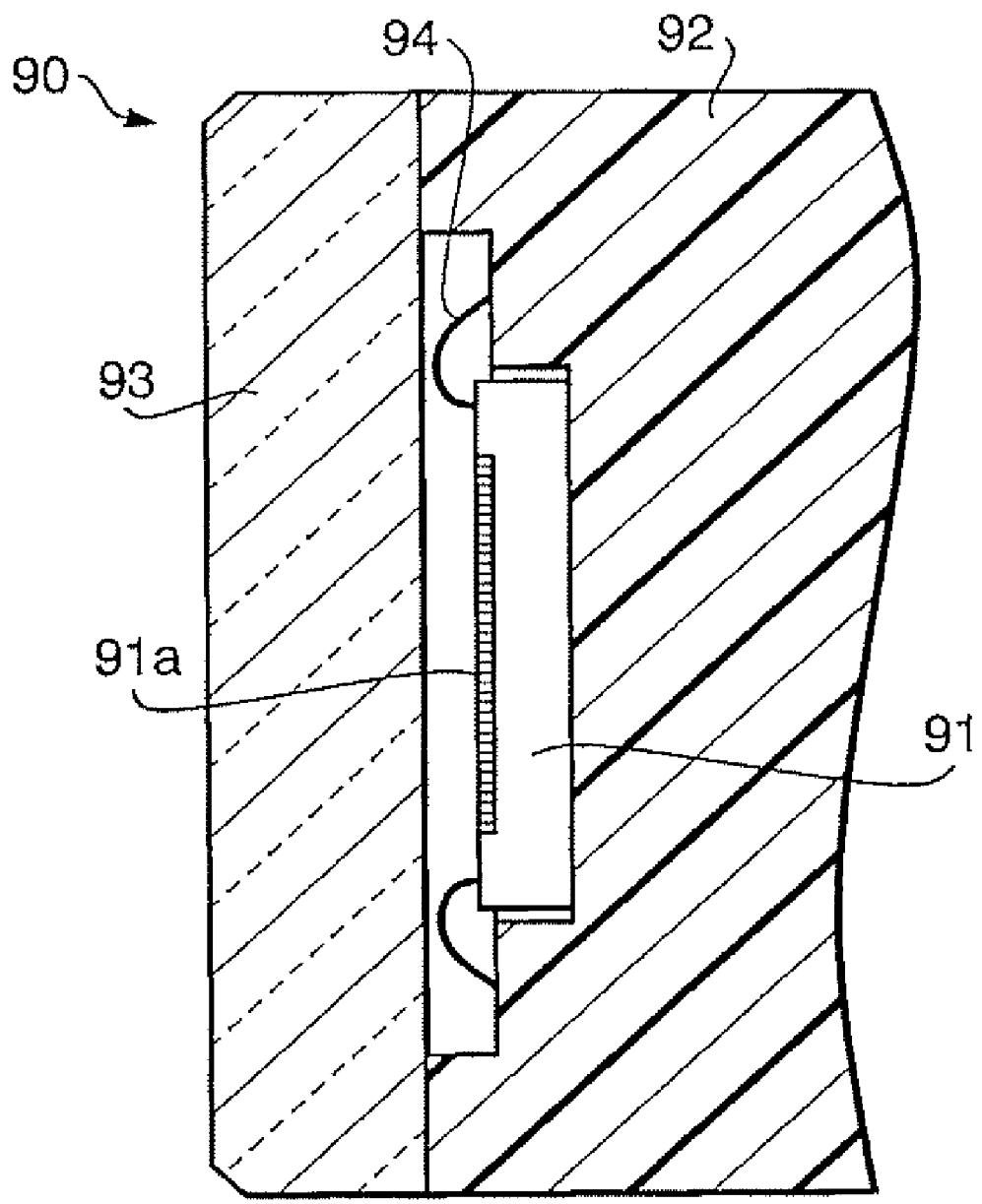
FIG. 8 is a cross-sectional side view of the conventional image capturing unit for the electronic endoscope when a disorder occurs.
Figure 9:
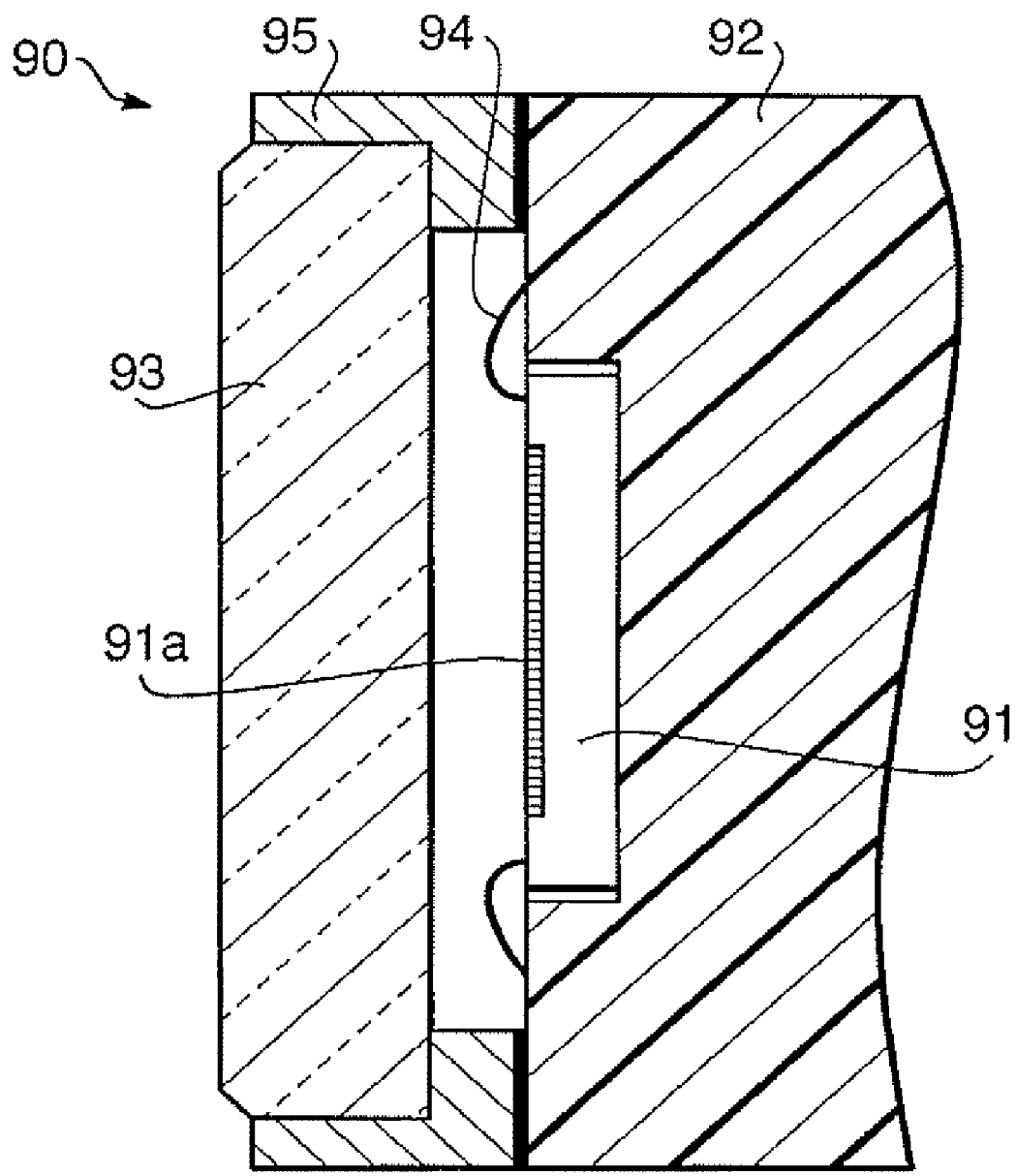
FIG. 9 is a cross-sectional side view of a second conventional image capturing unit for the electronic endoscope.
Figure 10:
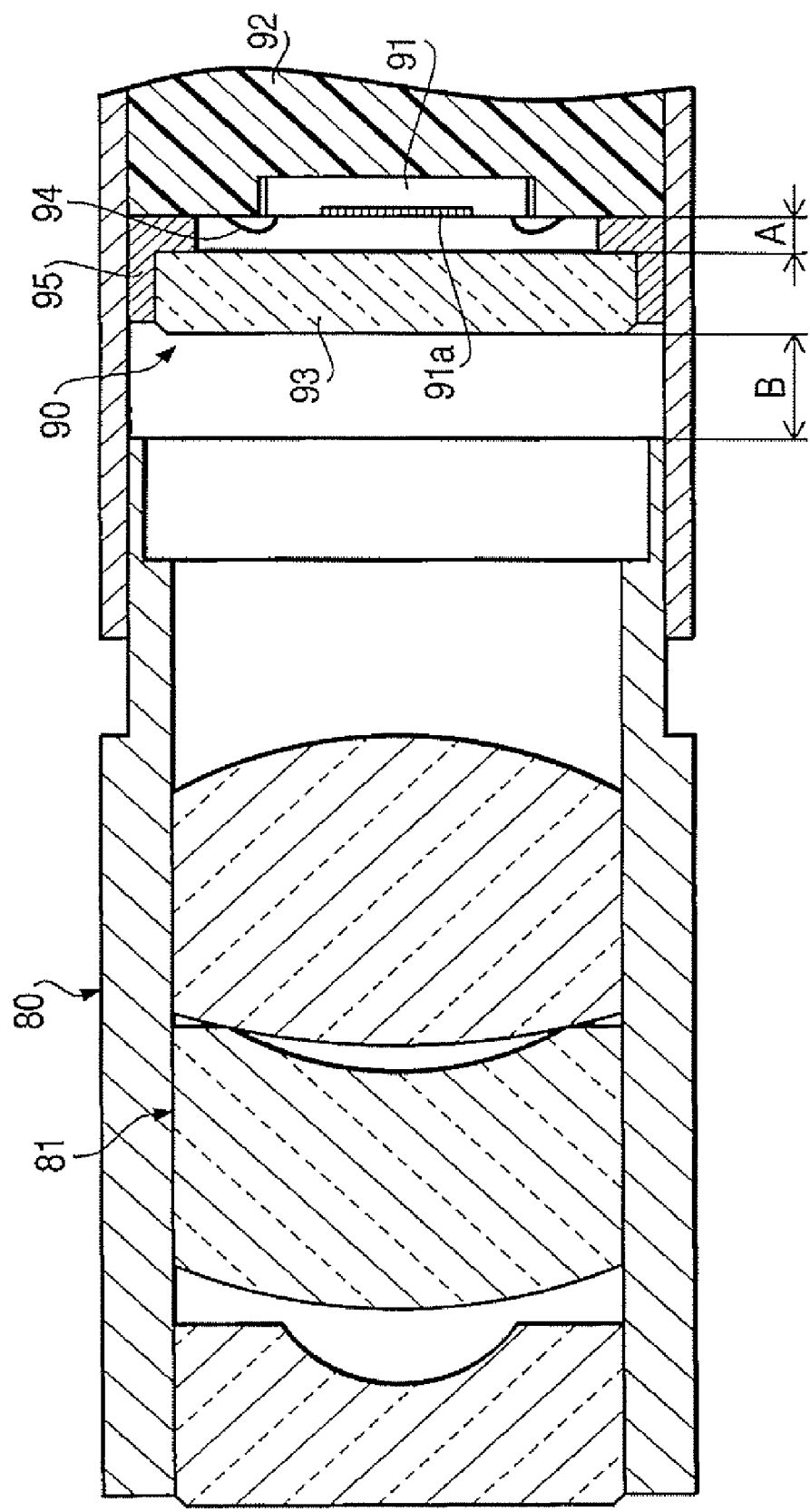
FIG. 10 is a cross-sectional side view of the second conventional image capturing unit for the electronic endoscope when incorporated in the objective optical system unit.
Figure 11:
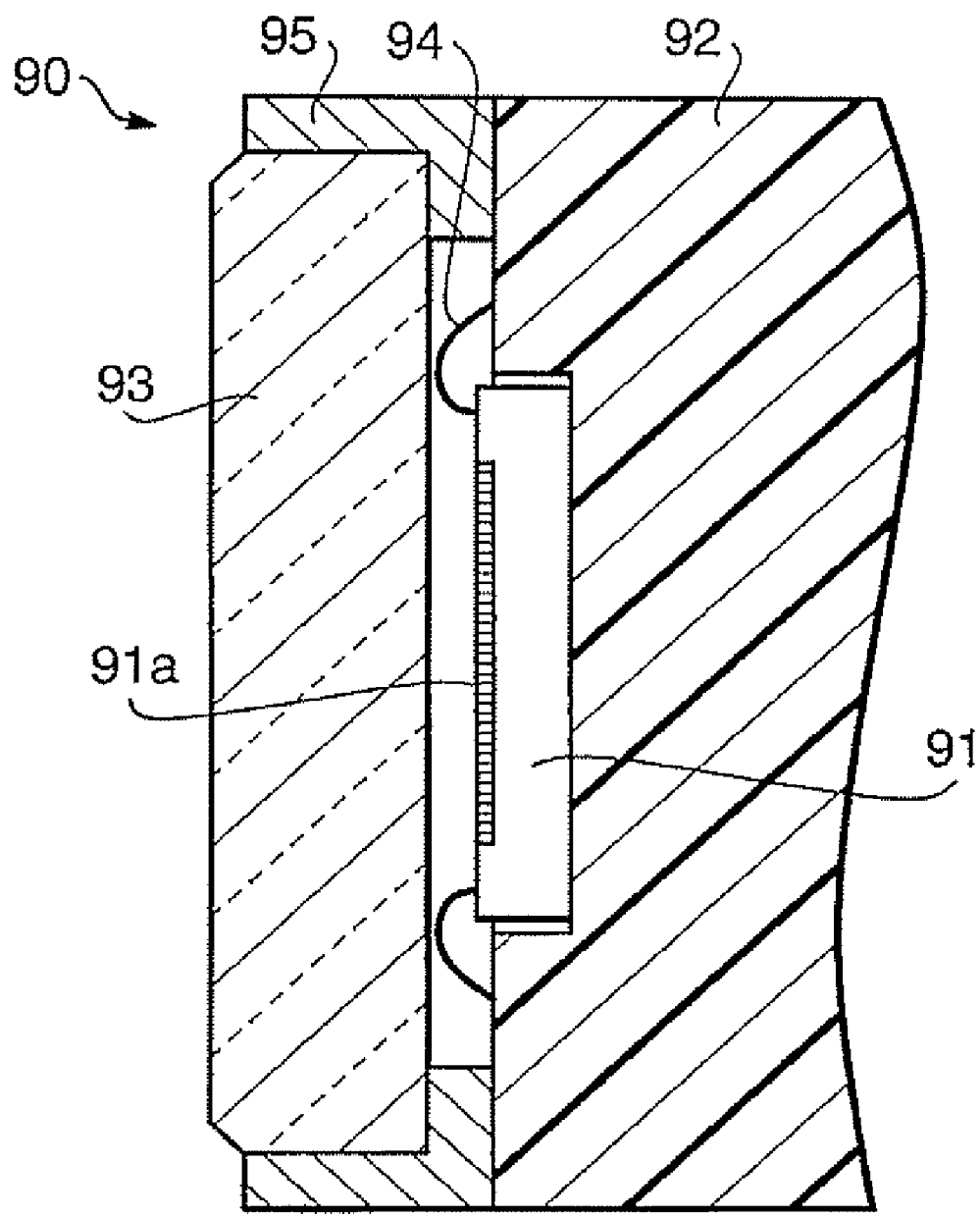
FIG. 11 is a cross-sectional side view of the second conventional image capturing unit for the electronic endoscope when a disorder occurs.

With the above-described configuration, the rear surface of the cover glass 15 does not contact the bonding wires 13. Therefore, the bonding wires 13 will not be damaged. Further, as shown in FIG. 5, when the image capturing unit 10A is implemented in the objective optical system unit 20 including the objective optical system 21, the distance A between tie image capturing surface 11a and the cover glass 15 is sufficiently small, and a sufficient back focus B for adjusting the focusing condition of the objective optical system 21 can be obtained.

The present disclosure relates to the subject matter contained in Japanese Patent Application No. 2005-201112, filed on Jul. 11, 2005, which is expressly incorporated herein by reference in its entirety,

What is claimed is:

1. An image capturing unit for an electronic endoscope, comprising:
  a solid-state image capturing element having multiple bonding wires arranged at peripheral positions on a front surface of the solid-state image capturing element, the bonding wires extending outward;
  an image capturing element holding frame having a front side surface formed with a recess in which the solid-state image capturing element is held; and
  a transparent cover glass provided at a tip end portion of the image capturing element holding frame and enclosing the front surface on the solid-state image capturing element from outside, wherein the tip end portion of the image capturing element holding frame is formed to have a tubular section having a substantially constant inner periphery with respect to a central axis of the tubular section as the tubular section extends from the front side surface, the cover glass being fitted in the tubular section and located at a position where the cover glass does not contact the bonding wires, air-tight cement being provided at a circumference of the glass cover such that no axial positioning structure, positioning the cover glass in the axial direction, engages a surface of the cover glass positioned within a periphery defined by the circumference of the cover glass, and wherein the cover glass is directly and air-tightly cemented on an inner surface of the tubular section of the holding frame.

2. The image capturing unit according to claim 1, wherein the cement comprises an inorganic adhesive agent.

* * * * *